United States Patent [19]
Eibofner et al.

[11] Patent Number: 6,102,704
[45] Date of Patent: Aug. 15, 2000

[54] METHOD AND DEVICE FOR THE DETERMINATION OF CARIES IN TEETH

[75] Inventors: Eugen Eibofner, Biberach; Markus Klotz, Bad Liebenzell, both of Germany; Adrian Lussi, Worb, Switzerland; Manfred Bareiss, Welzheim, Germany

[73] Assignee: Kaltenbach & Voigt GmbH & Co., Biberach, Germany

[21] Appl. No.: 09/034,843

[22] Filed: Mar. 4, 1998

[30] Foreign Application Priority Data

Mar. 7, 1997 [DE] Germany .......................... 197 09 500

[51] Int. Cl.$^7$ .................................................. A61C 5/00
[52] U.S. Cl. ............................ 433/215; 433/29; 433/229
[58] Field of Search ................................ 433/29, 215, 229

[56] References Cited

U.S. PATENT DOCUMENTS

| | | | |
|---|---|---|---|
| 4,479,499 | 10/1984 | Alfano | 433/29 X |
| 5,259,761 | 11/1993 | Schnettner et al. | 433/215 |
| 5,306,144 | 4/1994 | Hibst et al. | 433/29 |
| 5,382,163 | 1/1995 | Putnam | 433/215 |
| 5,851,113 | 12/1998 | Jung et al. | 433/29 |
| 5,874,677 | 2/1999 | Bab et al. | 433/215 X |
| 5,961,327 | 10/1999 | Lohn | 433/29 X |

FOREIGN PATENT DOCUMENTS

| | | |
|---|---|---|
| 30 31 249 C2 | 3/1981 | Germany . |
| 42 00 741 A1 | 7/1993 | Germany . |
| 93 17 984 | 5/1995 | Germany . |

*Primary Examiner*—Nicholas D. Lucchesi
*Attorney, Agent, or Firm*—Scully, Scott, Murphy & Presser

[57] ABSTRACT

Method and device for the detection of caries in teeth (8). In order, after investigation of a tooth (8), to be able again to find the tooth location with the greatest incidence of caries, the instantaneous measurement value and the peak measurement value—which corresponds to the location with the greatest incidence of caries attack—are displayed. By comparison of the instantaneous measurement value with the peak measurement value the tooth location with the greatest incidence of caries attack can be localised when the instantaneous measurement value coincides with the peak measurement value.

30 Claims, 4 Drawing Sheets

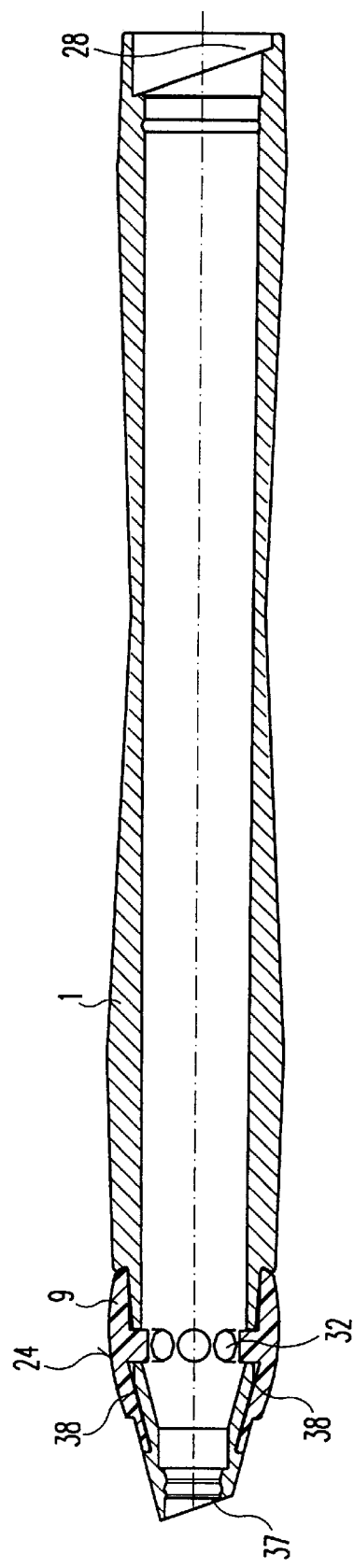

SELF-FLUORESCENCE OF THE TOOTH ENAMEL

METHOD AND DEVICE FOR THE DETERMINATION OF CARIES IN TEETH

BACKGROUND OF THE INVENTION

1. Technical Field

The present invention relates to a method and device for the determination of caries, plaque or bacterial infection in teeth.

2. Prior Art

As is known, caries in teeth can be detected by visual inspection or through the employment of X-rays. However, with a visual inspection, satisfactory results often cannot be achieved, since for example caries at an early stage or at a difficult to inspect tooth region cannot be determined. Because of the damaging effects of X-rays on human health, inspection with the aid of X-rays is not optimal.

There has thus been proposed a contactless investigation method for the determination of caries in teeth in which the tooth is irradiated with a virtually monochromatic light source. Due to the irradiation of the tooth with monochromatic light, a fluorescence radiation is excited at the tooth, whereby the fluorescence spectrum manifests clear differences between carious and healthy tooth regions. On the basis of the detected fluorescence spectrum of a tooth to be investigated, a healthy tooth region can thus be unambiguously distinguished from a carious tooth region. Corresponding dental devices for the recognition of caries are known for example from DE 30 31 249 C2, DE 42 00 741 A1 and DE 93 17 984 U1.

With the aid of such devices it can, however, only be determined whether the investigated tooth is carious or not. In the case of a carious tooth, with the known devices, for example a corresponding optical or acoustic indication is given. However, at a tooth recognised as carious, the degree of the caries attack can vary. After completion of the investigation it is however desirable to find again that location of the tooth which has the greatest degree of caries attack, in order to be able to treat the corresponding tooth location. This, however, is not possible with the known devices.

SUMMARY OF THE INVENTION

The present invention thus has the object of providing a method and a device for the recognition of caries in teeth with the aid of which the tooth location with the greatest caries attack can again be found, after a tooth has been recognised as carious.

This object is achieved by means of a method according to claim 1 and a device according to claim 6.

The subclaims describe advantageous configurations of the invention.

In accordance with the invention, during the investigation of a tooth for caries attack, the peak value of the fluorescence radiation excited at the tooth is determined and stored in each case. After the recognition that the investigated tooth is a carious tooth, the location having the greatest caries attack can be found again by renewed scanning of the tooth with the excitation radiation, in that the measurement value provided by the renewed irradiation is in each case compared with the peak value. If the instantaneous measurement value coincides with the stored peak value, the tooth location corresponding to this measurement value is the location with the greatest caries attack. The finding of the tooth location with the greatest caries attack can be facilitated in that during the renewed scanning an acoustic signal is generated the frequency of which increases with increasing measurement value, whereby in particular the acoustic signal is issued only so long as the measurement value increases. Alternatively, the acoustic signal may only be issued when the instantaneous value of the renewed investigation of the tooth coincides with the stored peak value.

It should be noted that the displayed peak value need not necessarily correspond to the maximum value of the excited fluorescence radiation, but may also be determined in some other way and derived from the fluorescence radiation.

Each tooth has a different self-fluorescence. Since this self-fluorescence can disrupt measurement, it is proposed in accordance with the invention to carry out a compensation procedure before the beginning of the measurement, whereby this compensation is effected by measuring a healthy tooth region. By the compensation, the counter or memory for the instantaneous measurement value is set to zero.

In accordance with the invention, different kinds of light probe should be available for investigation of a tooth, whereby the light probes are removably inserted onto a dental handpiece. After insertion of a new light probe onto the dental handpiece this must first be calibrated in accordance with the invention, whereby for this purpose the light probe is placed with its tip vertically on a reference object, e.g. a ceramics piece, and measured.

An exemplary embodiment of the invention will be described below in more detail, with reference to the drawings, which show:

DETAILED DESCRIPTION OF THE INVENTION

Figure 1:
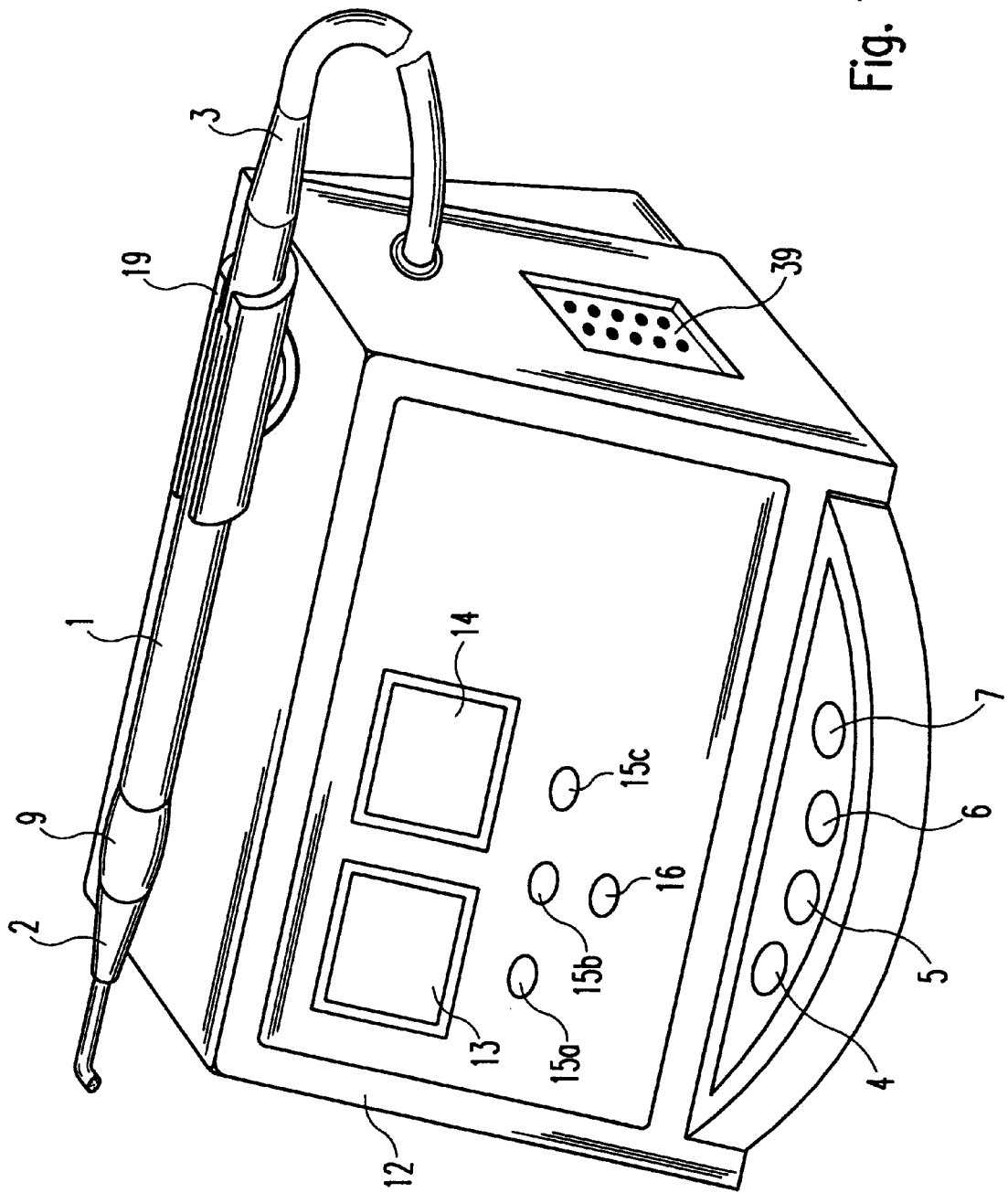
FIG. 1 an overall view of the device in accordance with the invention for the recognition of caries, FIG. 2 a simplified block circuit diagram of the internal structure of the device shown in FIG. 1, FIG. 3 a cross-sectional view of the dental handpiece employed with the device in accordance with the invention, FIG. 4a the calibration procedure of a light probe, and FIG. 4b the procedure of a compensation of the device in accordance with the invention for the recognition of caries.

FIG. 1 shows an overall view of the device in accordance with the invention for the recognition of caries, plaque or bacterial infection of teeth. The device in accordance with the invention can, however, be employed generally for the determination of an unhealthy tissue, the fluorescence radiation of which differs from that of a healthy tissue. Thereby, tooth tissue need not be involved: rather, a human or animal body tissue in general may be involved. The device shown in FIG. 1 includes a housing 12 which is connected via a supply hose 3 with a dental handpiece 1 and a light probe 2 inserted onto the dental handpiece. In order to reduce the weight of the device in accordance with the invention and to increase mobility, the device is advantageously supplied with a battery or an accumulator as voltage source. For this reason the front of the housing 12 has a light diode 16, with the lighting up of which the user's attention is drawn to the fact that the supply voltage has fallen below a particular limit value, whereby the user is requested to change the battery or charge the accumulator. Further, the device in accordance with the invention has three displays 15a–15c which identify the light probe 2 inserted onto the dental handpiece 1. In the present case, a selection can be made between three different light probes in dependence upon the nature of the tooth region to be investigated. The displays 13 and 14 serve for the display of the instantaneous fluorescence spectrum measurement value and of the peak value. As will be described in more detail below, the keys 4–7 serve inter alia for the selection of predetermined modes of operation and for selection of the light probe 2 inserted onto the dental handpiece 1. The dental handpiece 1 has a ring switch 9, whereby the ring switch 9 has a switching surface extending in the circumferential direction of the dental handpiece 1 in a ring shape, so that the ring switch 9 can be actuated simply by finger pressure regardless of the disposition of the dental handpiece in the hand of the operating person. The ring switch 9 serves in particular for switching the device on and off and deleting the peak value and for compensation of the light probe 2. For improving the transportability of the device in accordance with the invention, a holder 19 is provided into which the dental handpiece 1 with the light probe 2 can be placed. Advantageously, the housing 12 also has a (not shown) side recess into which the holder 19 can alternatively be inserted in order to be able to attach and place the dental handpiece 1 also to the side on the housing 12. The holder 19 is rotatable relative to the housing 12, whereby the rotation may be stepless or in correspondence to predetermined latching steps. Finally, the device may also have attachment means (e.g. on the base of the housing) in order to be able to attach it at a suitable location at a dental work station. The attachment can, for example, be effected with the aid of an angle piece which with receiving pins is attached to the device (for example in a receiving opening at the base of the device) and attached with an adhesive strip at a suitable location of a dental treatment station. By means of a suitable configuration of the angle piece, the device may be rotated or tilted in horizontal and vertical direction and thus optimally adapted to the angle of view of the user. Further, screw attachments may be considered.

Figure 2:
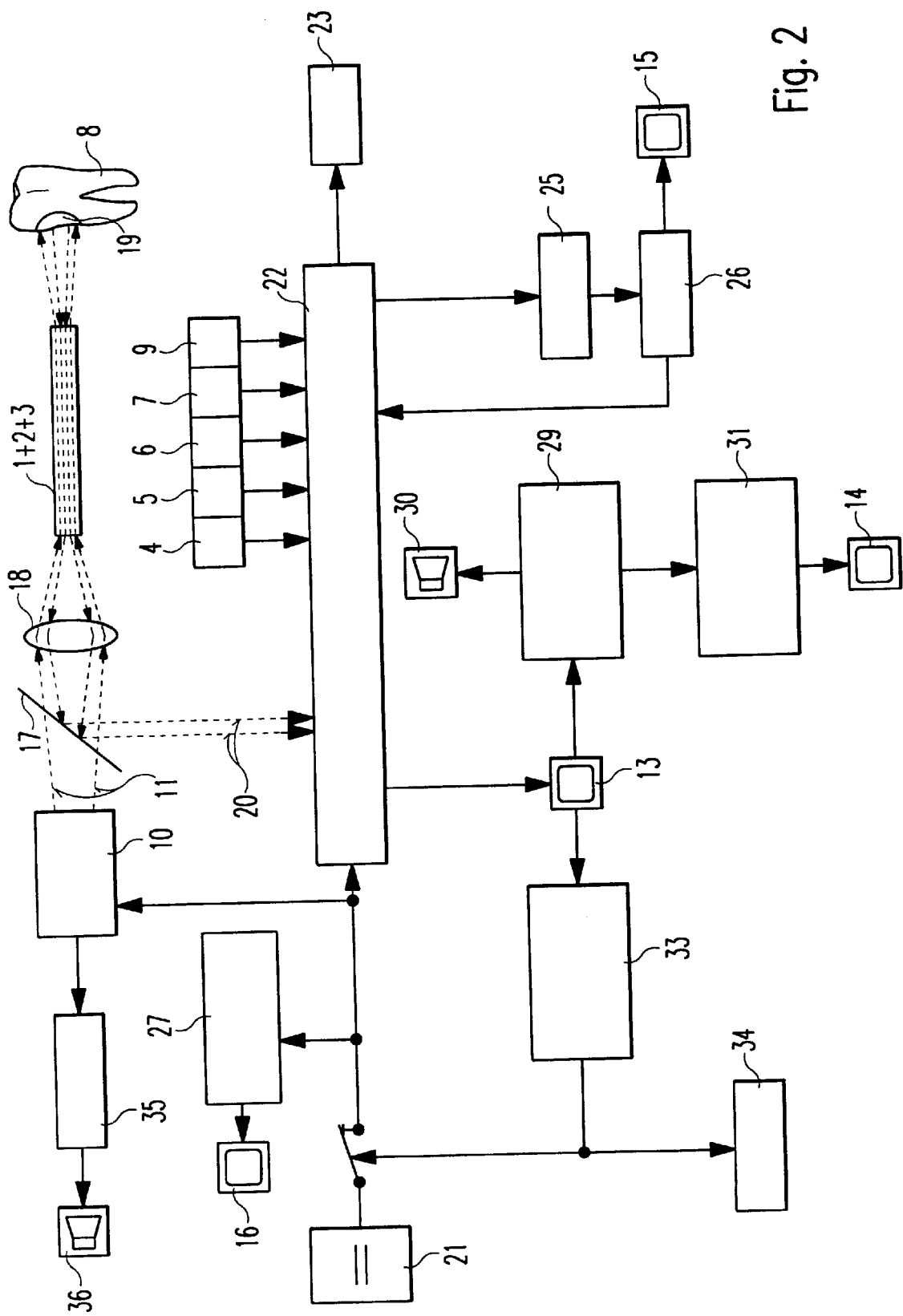

The functioning of the device in accordance with the invention shown in FIG. 1 will be described in more detail below with reference to FIG. 2.

As already explained, the device in accordance with the invention is a device which detects caries in teeth with the aid of irradiation of a tooth 8 to be investigated. The light source 10 generating the excitation light may for example be a HeNe laser or a laser diode, which advantageously generates the excitation radiation 11 with a wavelength in the range 600 nm to 670 nm. In particular, an excitation wavelength of ca. 655 nm is advantageous. The excitation radiation 11 is coupled into the light conductor system including the connection hose 3, the dental handpiece 1 and an light probe 2 via a lens system 18 or collimator optics, frequently already integrated in the case of laser diodes. With the aid of the light conductor system, the excitation radiation 11 is delivered in an aimed fashion to a region 19 of the tooth 8 to be investigated. Due to the excitation radiation there is brought about in the irradiated tooth region 19 a fluorescence radiation 20 over a relatively broad spectral range, which fluorescence radiation is acquired by detection fibers provided in the light probe 2 and delivered via a beam divider 17 to an optical filter of a photodiode for detecting the fluorescence radiation, the output signal of which is in turn delivered to a central unit 22. The optical filter and the photodiode are not shown in FIG. 2 since they can also be integrated in the central unit 22. Advantageously, the dental handpiece 1 has a central core light conductor for guiding the excitation radiation 11, which is surrounded by a plurality of coaxially arranged detection light conductor fibers for leading off the acquired fluorescence radiation, whilst the light probe 2 has a plurality of emission fibers for irradiating the tooth 8 with the excitation radiation and a plurality of detection fibers for acquiring the fluorescence radiation returned from the tooth, whereby the detection and emission fibers of the light probe 2 are connected with the corresponding detection fibers and the central core light conductor. The instantaneous measurement value corresponding to the fluorescence radiation received by the central unit 22 is shown in a display 13. On the basis of an increased display value, the dentist can deduce that the investigated tooth 8 is a carious tooth. The exact sequence of operation of the device for the recognition of caries in accordance with the invention shown in FIG. 2 is as follows.

Figure 4A:
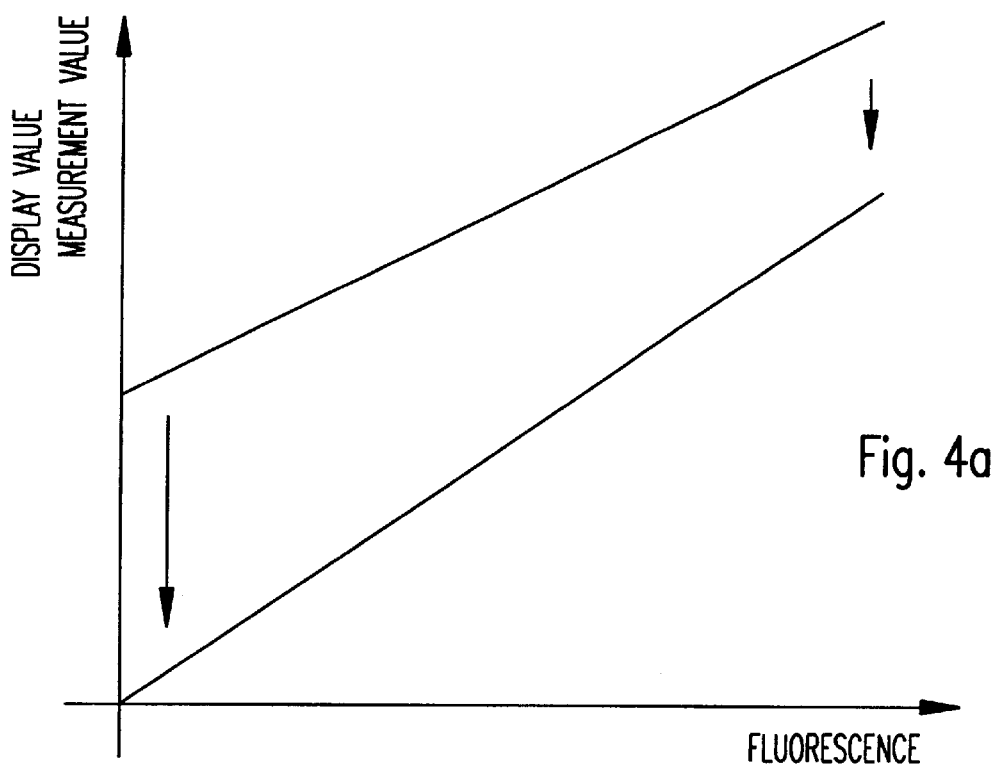

Initially, a particular light probe 2 is placed on the dental handpiece 1. In the present case, a selection can be made from three different light probes for example for the investigation of smooth tooth surfaces, spaces between teeth, or fissures. If a light probe is newly placed on the dental handpiece 1, the corresponding light probe can first be calibrated. For this purpose, the selected light probe is placed vertically with its tip on two reference objects or calibration standards having different fluorescence values. The reference objects may for example be made of ceramics. The calibration mode is initiated by pressing the key 4, whereby the key 4 must be held pressed until the central unit 22 issues an acoustic confirmation signal. After successful calibration with regard to the first reference object, calibration with regard to a second reference object is effected in similar manner. The procedure of the calibration is illustrated by way of example in FIG. 4a. From there it can be seen that with the aid of the calibration the original measurement curve for the selected light probe is transformed into a measurement curve which develops directly proportional to the fluorescence, whereby the displacement of the original measurement curve is derived through the calibration of the two reference objects and the calibration standard values obtained therefrom. The calibration standard values yielded by the calibration are stored in a memory 23. If one of the two calibration standards or reference objects is exchanged, the corresponding calibration standard value of the new reference object must be newly set. For this purpose, the key 5 is again pressed and then, via the ring switch 9, the previously set calibration standard value altered, After alteration of the new calibration standard value this is stored anew in the memory 23.

The type of light probe inserted onto the dental handpiece 1 must first be indicated to the device before the actual beginning of the measurement. This is effected by actuation of the key 6 whereby, in dependence upon the selection, of one of the three light diodes 15a–15c of the housing 12 lights up.

Figure 4B:
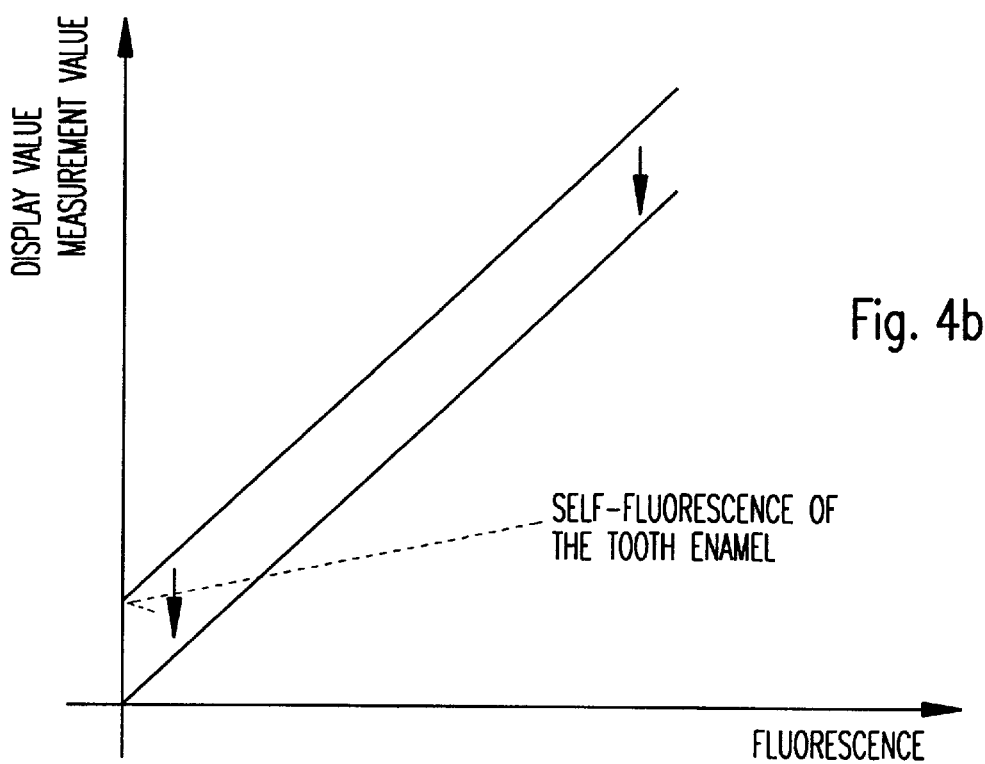

In accordance with the invention, before being put into operation, each light probe 2 is compensated with reference to the self-fluorescence of the tooth to be investigated. Since each tooth has a different self-fluorescence, the self-fluorescence can disrupt the measurement. Thus, for compensation, before the beginning of the actual caries recognition, a healthy tooth is measured with the selected light probe 2. The compensation procedure is initiated by a long press (for example for one second) of the ring switch 9 on the dental handpiece 1. With the compensation the instantaneous measurement value display 13 is set to zero. The compensation procedure is illustrated, in an example, in FIG. 4b. From this it can be seen that with the aid of the compensation procedure the offset caused by the self-fluorescence of the tooth to be investigated can be removed.

The compensation values for each light probe 2 are stored in a memory 25, whilst after selection of a particular light probe the corresponding light probe type and the corresponding compensation value are read out into a memory 26 and then employed for the actual measurement.

As already mentioned, during the actual measurement operation there is displayed in the display 13 the respective instantaneous measurement value for the fluorescence radiation excited at the investigated tooth 8. However, an acoustic indication of the measurement value is also conceivable. The instantaneous value is compared in each case with the previously determined peak value (circuit element 29) and, if the instantaneous value exceeds the previous peak value, is stored in a peak value memory 31 as new peak value and shown in the display 14. The display 14 thus always shows the peak value of the caries measurement so far determined. The peak value can be deleted at any time by a short double click, i.e. a double actuation within a predetermined interval of time, of the ring switch 9. After completion of a first investigation of the tooth 8 it can thus be determined whether the investigated tooth is carious and the measurement value corresponding to the tooth location with the greatest incidence of caries attack is displayed as peak value in the display 14.

After completion of the investigation of the tooth 8, for actual treatment of the carious location of the tooth 8, one must be able to again find the tooth location having the greatest incidence of caries attack. In accordance with the invention, this is achieved in that the tooth 8 is again scanned with the excitation radiation 11 and the instantaneous measurement value shown in the display 13 compared with the peak value of the display 14. The comparison may be effected visually or automatically. If the instantaneous measurement value shown in the display 13 corresponds to the peak value shown in the display 14, the tooth location with the greatest incidence of caries attack has again been found. In order to facilitate the finding of the tooth location most heavily attacked by caries it is proposed in accordance with the invention to emit via a loudspeaker an acoustic signal the frequency of which rises or falls with changed measurement value, upon the renewed scanning of the tooth 8. Alternatively it can be provide that this acoustic signal is only emitted so long as the measurement value increases. In this way the location with the greatest incidence of caries attack can be particularly quickly located. It can also be provided that the acoustic signal is first emitted when the measurement value shown in the display 13 corresponds to the peak value shown in the display 14. By way of the key 17 of the housing 12, shown in FIG. 1, the different acoustic signal modes can be selected. In particular, the issue of the acoustic signal can also be turned off via this key 7.

As already explained, the device for the recognition of caries in accordance with the invention is advantageously operated with a battery or accumulator 21 as voltage source. During operation, the supply voltage delivered by the voltage source 21 is regularly checked by a corresponding monitoring device 27 and, if the supply voltage has fallen below a predetermined limit value, the light diode 16 provided in the housing 12 is switched on. In order to conserve the voltage source 21, the device in accordance with the invention has an automatic off function 33 which interrupts the voltage supply if—over a predetermined interval of time—no measurement is carried out or no key is actuated.

Further, a device 34 for detection of the total operating time of the device in accordance with the invention may be provided.

In order to be able to recognise an aged or defective laser 10, there is additionally provided a device 35 which continuously monitors the laser current of the laser 10 and issues a corresponding warning signal via a loudspeaker 36 if the detected laser current lies below a predetermined limit value or exceeds a predetermined limit value.

Attention is directed to the fact that the memories 23, 25 and 26 are constituted as non-volatile memories so that the calibration standard values, compensation values and the type of the last-used light probe stored therein are retained even after switching off of the device. Thus, upon a new start of the device in accordance with the invention, work can continue with the same settings as before switching off of the device.

Finally, FIG. 3 shows a cross-sectional view of the dental handpiece shown in FIG. 1, whereby in particular the ring switch 9 is illustrated in detail. This ring switch 9 includes an actuation surface 24 which extends ring-like around the dental handpiece 1, which actuation surface is supported inwardly against contact springs 38. By pressing the actuation surface 24, contact means 32 are activated which, in dependence upon the set operating mode, carry out the above-described functions. The pressed actuation surface 24 is, after its release, urged outwardly back into the initial position by the contact springs 38. The ring switch 9 shown in FIG. 3 has the advantage that the switch can be simply actuated by a single finger press, regardless of the disposition of the handpiece in the hand of the dentist. At its two longitudinal ends, the dental handpiece 1 has hollow spaces 37 and 28 for receiving the light probe and the supply hose.

In order to be able to process the fluorescence measurement values acquired by the device in accordance with the invention by computer, a suitable interface 39 for data transmission to an external computer (personal computer) may be provided. In particular, for data transmission, an optical coupler can be used instead of an electrical data transfer path.

What is claimed is:

1. A method of investigating teeth for determining the presence of caries, plaque or bacterial infections, comprising the steps of: irradiating an investigated tooth (8) with an excitation radiation (11), determining an instantaneous measurement value of a fluorescence radiation (20) produced at the tooth by the excitation radiation, comparing the instantaneous measurement value with a peak measurement value of the fluorescence radiation determined during the measurement operation, which defines a tooth region of the investigated tooth having the highest incidence of a caries attack, and localizing the defined tooth region with the highest incidence of caries attack, when the instantaneous measurement value coincides with the peak measurement value.

2. A method according to claim 1, wherein the peak measurement value is determined by the steps of:
   a) detecting an instantaneous measurement value of the fluorescence radiation (20) produced at the tooth (8) by the excitation radiation (11),
   b) comparing the instantaneous measurement value with a previous peak measurement value and storing the instantaneous measurement value as a new peak measurement value when the instantaneous measurement value is greater than the previous peak measurement value, and repeating steps a) and b) until the end of the measurement.

3. A method according to claim 1, wherein a compensation is effected prior to the beginning of the measurement, through which the measurement is adapted to an inherent fluorescence of the tooth (8), and wherein the instantaneous measurement value is set to zero.

4. A method according to claim 3, wherein the fluorescence radiation is acquired by first acquisition means (2), and prior to AN application of subsequent acquisition means, there is effected a calibration of the subsequent acquisition means on the basis of two predefined reference objects.

5. A method according to claim 4, wherein the calibration is effected in a calibrating operation by a switching element (9), effecting the compensation in a measurement operation by said switching element (9) whereby the switching element is actuated for a specific period of time, and deleting during the measurement operation a stored peak measurement value when said switching element (9) is actuated several times within a predetermined interval of time.

6. An electrically-operated device for determining the presence of caries, plaque or bacterial infections of teeth, said device comprising means (1) for generating an excitation radiation (11) irradiating an investigated tooth (8), acquisition means (2) for acquiring an instantaneous measurement value of a fluorescence radiation (20) produced at the tooth by the excitation radiation, and memory means (31) for storing a peak measurement value of the acquired fluorescence radiation (20) attained over a specified measurement period.

7. A device according to claim 6, comprising display means (13,14) for displaying an instantaneous measurement value and the peak measurement value of the fluorescence radiation attained over the specified measurement period.

8. A device according to claim 6, comprising means (9) for erasing the memory means (31) storing the peak measurement value.

9. A device according to claim 8, wherein the means for erasing the memory means (31) storing the peak measurement value and the means for compensation of the device comprises a single switching element (9) having the functioning thereof determined in dependence upon the duration of switching actuation and sequence of switching actuation.

10. A device according to claim 9, wherein the switching means (9) is constituted of a switch which extends with a switch surface in a ring-shape around a dental handpiece (1), wherein the dental handpiece (1) serves for directing the excitation radiation (11) and carrying the acquisition means (2).

11. A device according to claim 6, comprising compensating, means (9) for the device to adapt the device to an inherent fluorescence of the tooth (8).

12. A device according to claim 6, comprising means (1) for calibrating the acquisition means (2) on the basis of selectively one reference object or two reference objects which are formed of a ceramic material.

13. A device according to claim 6, comprising a holder (19) for a dental handpiece (1) of the device, said holder being attachable to a housing (12) of the device and said holder being selectively rotatable in increments or steplessly.

14. A device according to claim 6, wherein said acquisition means (2) are exchangeable, and including display means (15a–15c) for the display of respectively selected acquisition means.

15. A device according to claim 14, comprising means (6) for selecting the acquisition means (2).

16. A device according to claim 14, comprising memory means (26) for storing the last selected acquisition means (2).

17. A device according to claim 14, comprising memory means (25) for storing the compensation values of the individual acquisition means (2).

18. A device according to claim 14, comprising memory means (23) for storing the calibration values of individual of the acquisition means (2).

19. A device according to claim 6, comprising means (16) for emitting a warning signal when a supply voltage of the device has fallen below a specified limiting value.

20. A device according to claim 6, comprising means (33) for the automatic switching off of a voltage supply (21) of the device, and activating the supply voltage, when the device is not actuated within a specified time interval.

21. A device according to claim 6, comprising means (34) for determining the total operating time of the device.

22. A device according to claim 6, wherein the means (10) for generating the excitation radiation (11) generate laser light as the excitation radiation, and inclding means (35) for monitoring the laser current of the means (10) generating the laser light which generate a warning signal upon the laser current falling below a specified limiting value or increasing above a specified limiting value.

23. A device according to claim 6, comprising means (30) for emitting an acoustic signal in dependence upon the instantaneous measurement value, whereby the frequency of the signal increases with the instantaneous measurement value.

24. A device according to claim 23, wherein the acoustic signal is emitted only at an increase in the instantaneous measurement value.

25. A device according to claim 23, wherein the acoustic signal is emitted only at a coincidence of the instantaneous measurement value with the peak measurement value.

26. A device according to claim 6, comprising means (39) for the transmission of the measurement values acquired by the acquisition means (2) to a therewith connectable computer.

27. A device according to claim 26, wherein the transmission means (39) include an optical coupler.

28. A device according to claim 6, wherein a voltage supply device (21) which delivers a supply voltage for the operation of the device selectively consists of an accumulator or a battery.

29. A device according to claim 6, comprising attachment means for mounting the device at a dental work station.

30. A device according to claim 29, wherein the attachment means are configured to enable a rotational or tilting movement of the device at the work station.

* * * * *